United States Patent [19]
Wei

[11] Patent Number: 5,750,820
[45] Date of Patent: May 12, 1998

[54] MULTIPLE GRADE FLUSH ADSORPTION SEPARATION PROCESS

[76] Inventor: Chiu N. Wei, 15707 Crestbrook, Houston, Tex. 77059

[21] Appl. No.: 584,163

[22] Filed: Jan. 11, 1996

Related U.S. Application Data

[63] Continuation of Ser. No. 121,680, Sep. 15, 1995, abandoned.

[51] Int. Cl.⁶ .................................................. C07C 7/12
[52] U.S. Cl. ........................ 585/826; 585/820; 585/821
[58] Field of Search ............................ 585/820, 821, 585/826

[56] References Cited

U.S. PATENT DOCUMENTS

| | | |
|---|---|---|
| 3,040,777 | 6/1962 | Carson et al. . |
| 3,201,491 | 8/1965 | Stine et al. . |
| 3,205,166 | 9/1965 | Ludlow et al. . |
| 3,268,605 | 8/1966 | Boyd, Jr. et al. . |
| 3,422,848 | 1/1969 | Liebman et al. . |
| 3,696,107 | 10/1972 | Neuzil .................. 260/674 SA |
| 3,706,812 | 12/1972 | Rosset et al. . |
| 3,761,533 | 9/1973 | Otani et al. . |
| 4,029,717 | 6/1977 | Healy et al. . |
| 4,031,156 | 6/1977 | Geissler et al. . |
| 4,108,915 | 8/1978 | Rosback et al. .................. 260/674 SA |
| 5,183,540 | 2/1993 | Rubin . |

FOREIGN PATENT DOCUMENTS

| | | |
|---|---|---|
| 0096567 | 12/1983 | European Pat. Off. . |
| 1417641 | 10/1968 | Germany . |

Primary Examiner—Glenn Caldarola
Assistant Examiner—In Suk Bullock
Attorney, Agent, or Firm—Edward F. Sherer

[57] ABSTRACT

A process for separating a product from a multicomponent feedstream to an adsorption apparatus or system. The apparatus or system may comprise a moving-bed or a simulated moving-bed adsorption means. The product comprises at least one organic compound, such as an aryl compound with alkyl substitutes. The conduits used to supply the feedstream to the apparatus or system are flushed with media of multiple grades. Amounts of the media are sufficient to fill the conduits. The process achieves improvements in the efficiency of adsorption separation, the capacity of adsorption apparatus and systems, and the purity of product attainable by adsorption process.

49 Claims, 5 Drawing Sheets

MULTIPLE GRADE FLUSH ADSORPTION SEPARATION PROCESS

This application is a continuation of application Ser. No. 08/121,680, filed Sep. 15, 1995 now abandoned.

BACKGROUND OF THE INVENTION

1. Field of the Invention

The invention relates to a process for separating one or more of the components from a multicomponent fluid mixture. In particular, it relates to a process for separating organic compounds from such a fluid mixture by means of adsorption apparatus, such as moving-bed or simulated moving-bed adsorption apparatus, or a system comprising such apparatus.

2. Description of Related Art

Various means are currently available to separate the components of a multicomponent fluid mixture. If the densities of the components differ sufficiently, the effects of gravity over time may be adequate to separate the components. Depending on the quantities of the components involved, a centrifuge may be used to more rapidly separate components with different densities. Alternatively, distillation may be used to separate components with different boiling points. Nevertheless, some fluid mixtures comprise components which have similar boiling points, and in such cases, separation by distillation may be a difficult and an inefficient means to separate these components. Too many contaminants, e.g., unwanted components, also may evaporate along with (or fail to evaporate from) the desired component(s), or the separation may require high energy expenditures due to the recycling through the distillation process that may be necessary to attain a desired degree of separation or purity. Therefore, in view of the deficiencies of these processes, adsorption often has been preferred as a process for separating the components from a multicomponent fluid mixture to obtain relatively pure products.

An adsorption apparatus or system operates by contacting the fluid mixture with an adsorbent material, e.g., adsorbent solids, to effect separation. Upon contact of the fluid with the material, a physical attraction occurs, and bonds form between the material and a selected component or components of the fluid. Typically, the material is a bead-like solid and often, the solid is spherical which makes such materials easy to handle and to put inside vessels, e.g., sieve chambers, for use in an adsorption-separation process (hereinafter an "adsorption process").

The efficiency of an adsorption process may be partially dependent upon the amount of the surface area of the adsorbent solids which is available for contact with a fluid mixture. The surface area available may be more than just the superficial, external surface of the solids. Suitable solids also may have internal spaces. Such internal spaces may comprise pores, channels, or holes in the surface of the solids and may run throughout the solids, much as in sponges. Thus, the fluid contacts not only the superficial surface, but penetrates into the solids. Sieve chambers increase the contact surface between the fluid and the solids in an adsorption process by concentrating them in a confined space. Such structures often are described as molecular sieves, and the volumetric amount of components that may be adsorbed by a molecular sieve is termed the molecular sieve capacity.

In an adsorption process, separation of the fluid components may be accomplished because the material may have a physical attraction for one or more of the components of the mixture in preference to other components of the mixture. Although all of the components of a mixture may be attracted in varying degrees to the material, there is a preference engineered into the process, such that predominantly the desired component(s) may be attracted and remain with the material in preference over all others. Therefore, even if less preferred components of a mixture initially come into contact with a portion of the material, because of the stronger attraction of the material for the desired component(s) of the mixture, the less preferred component(s) may be displaced from the material by the desired, and more strongly preferred, component(s). Therefore, although the fluid mixture entering a sieve chamber might be composed of multiple components, the fluid mixture initially leaving the vessel would be composed largely of the components which had been less preferentially adsorbed into the material.

In adsorption processes using adsorbent solids, separation occurs for a period of time, but eventually all the available surface sites on and in the solids are taken up by the desired component(s) or are blocked by concentrations of unwanted components. At that point, little significant additional adsorption of component(s) from the mixture is likely to occur, and the fluid mixture which might be withdrawn from the chamber may be insignificantly changed by further exposure to the solids. Therefore, the adsorption step of the process is ended, and the component(s) which have been adsorbed by the solids must be removed from the solids, so as to effect separation and permit reuse of the solids.

A suitable adsorption apparatus or system might first permit adsorption of a product comprising the desired component(s) by the solids and later treat the solids to cause them to release the product and permit recovery of this product. Such an adsorption apparatus or system might comprise a "moving-bed" which permits movement of a tray or bed of the solids through a chamber, such that at different locations, the solid is subjected to different steps of an adsorption process, e.g., adsorption, purification, and desorption. These steps are defined in greater detail below. Nevertheless, moving the solids through an adsorption apparatus may be difficult and involve complex machinery to move trays or beds. It also may result in loss of the solids by attrition. To avoid these problems, some adsorption apparatus and systems have been designed to "simulate" moving the tray(s) or bed(s) to the locations, e.g., zones, of different steps of an adsorption process. Simulation of the movement of the tray(s) or bed(s) may be accomplished by use of a system of conduits which permits directing and redirecting the streams of fluids into the chamber at different zones at different times. As these stream changes occur, the solids are employed in different steps in an adsorption process as though the solids were moving through the chamber.

The different zones within an adsorption apparatus or system are defined by the particular step of the adsorption process performed within each zone, e.g., (1) an adsorption step in the adsorption zone; (2) a purification step in the purification zone; (3) a desorption step in the desorption zone. A more detailed explanation of the zones of the adsorption process follows:

Adsorption Zone. When a multicomponent fluid feedstream is fed into the adsorption apparatus or system, the portion of the apparatus or system into which the feedstream is being fed is termed an "adsorption zone." In the adsorption zone, the fluid comes into contact with the adsorbent material, and the desired component(s) are adsorbed by the adsorbent material. As noted above, other components may also be adsorbed, but preferably to a lesser extent. This preferential adsorption may be achieved by the selection of an adsorbent material, e.g., adsorbent solids, which has a preference for adsorbing the desired component(s) from the multicomponent feedstream. Although only the desired component(s) may have been adsorbed by the solids, other less preferentially adsorbed components of the fluid mixture may still remain in void spaces between the solids and possibly, in the pores, channels, or holes within the solids. These unwanted components preferably are removed from the solids before the desired component(s) are recovered from the solids, so that they are not recovered along with the product.

Purification Zone. After adsorption, the next step is to purify the fluid and adsorbent material in the chamber. In this step, the tray(s) or bed(s) may be moved or flow within the conduits may be changed, so that the multicomponent feedstream may no longer be fed into the adsorption zone. Although the tray(s) or bed(s) have not moved, the material may now be described as being in a "purification zone" because a fluid stream, e.g., a purification stream, is fed into the adsorbent material to flush the unwanted components from the adsorbent material, e.g., from within and from the interstitial areas between the solids. Thus, a fluid comprising unwanted components, i.e., raffinate, is flushed from the purification zone by substituting a fluid comprising the desired component(s) or other component(s) deemed to be more acceptable for the unwanted components. The unwanted components may be withdrawn in a raffinate stream. Because an objective of the adsorption process may be to separate the product comprising the desired component (s) from other components which may have nearly the same boiling point or density as the desired component(s), purification may displace, unwanted components and substitute another fluid which can be more readily separated by other means, e.g., distilled.

Desorption Zone. After the solids have been subjected to the purification stream, the stream in the conduit(s) may again be changed to introduce a desorbent steam into the chamber to release the product. The desorbent stream contains desorbent which is more preferentially adsorbed by the solids than the product comprising the desired component (s). The desorbent chosen will depend in part upon the desired component(s), the adsorbent materials, and the ease with which the desorbent can be separated from the product. Once the desorbent stream has been introduced to the chamber, the product may be withdrawn from the chamber.

Each and every step and zone might be present somewhere in an adsorption apparatus or system if simultaneous operations are conducted. Nevertheless, the steps may be performed successively or staggered over time. Further, in some adsorption processes, the unwanted components may be adsorbed, and the product comprising the desired component(s) allowed to pass through the adsorption apparatus or system. Therefore, the terms raffinate and extract are relative and may depend upon the particular nature of the components being separated, the preference of the solids, and the nature of the apparatus or system. Although the present invention will be discussed primarily in terms of apparatus and systems in which the product is adsorbed by the solids, the invention is not limited to such configurations.

As noted above, an apparatus suitable for accomplishing the adsorption process of this invention is a simulated moving-bed adsorption apparatus. Typically, such an adsorption apparatus may be contained in a vertical chamber. Such a chamber may be packed with adsorbent solids, possibly in trays or beds stacked within the chamber. More than one type of solid also might be used. The chamber also may have the capability to perform each of the above-described steps simultaneously within different locations, e.g., zones, in the chamber. Thus, the composition of the fluid in the chamber may vary between zones although there may be no structures completely separating these zones. This may be achieved by the use of a serially and circularly interconnected matrix of fluid communication conduits including associated means, such as valves and pumps, which permit streams to be directed and redirected into different zones of the chamber and to change the direction of these streams through the solids within the different zones of the chamber. The different zones within the chamber may have constantly shifting boundaries, as the process is performed.

The cyclic advancement of the streams through the solids may be accomplished by utilizing a manifold arrangement to cause the fluid to flow in a counter current manner with respect to the solids. The valves in the manifold may be operated in a sequential manner to effect the shifting of the streams in the same direction as overall fluid flow throughout the adsorbent solids. See U.S. Pat. No. 3,706,812, the disclosure of which is incorporated herein by reference. Another means for producing a countercurrent flow in the solid adsorbent is a rotating disc valve by which the streams, e.g., feed, extract, desorbent, and raffinate, and line flush, are advanced cyclically in the same direction through the adsorbent solids. Both U.S. Pat. Nos. 3,040,777 and 3,422,848 disclose suitable rotary valves. Both suitable manifold arrangements and disc valves are known in the art.

In many instances, one zone may contain a larger quantity of adsorbent material than other zones. Moreover, zones other than those discussed above may also be present. For example, in some configurations, a buffer zone between the adsorption zone and the desorption zone may be present and contain a small amount of adsorbent material relative to the zones surrounding it. Further, if a desorbent is used that can easily desorb extract from the adsorbent material, only a small amount of the material need be present in the desorption zone in comparison to the other zones. In addition, the adsorbent need not be located in a single chamber, but may be located in multiple chamber or a series of chambers.

In a simulated moving-bed apparatus or system, means for introducing and withdrawing fluids may comprise a plurality of fluid communication conduits. Nevertheless, the same fluid communication conduit may be used in a first instance to input a feedstream into the apparatus or system and later to withdraw an extract stream. This could result in reduced product purity due to contamination of the withdrawn product. Fluid communication conduits may contain unwanted components, such as residue remaining in the conduit from earlier additions or withdrawals of streams. This problem may be overcome by employing separate conduits for each stream or by removing such residue from the conduits by flushing them with a medium which would not effect product purity as adversely as would a unwanted component remaining in the fluid communication conduit. Because the flushing medium could be an unwanted component, however, a preferred flushing medium has been the product or the desorbent, which might be more readily separated downstream of the chamber than would the residue. See U.S. Pat. No. 4,031,156. Nevertheless, flushing conduits with the product reduces the output of the adsorption process.

The process of an embodiment of the present invention employs the simulated countercurrent flow processes described in U.S. Pat. Nos. 3,201,491; 3,761,533; and 4,029,717, the disclosures of which are incorporated herein by reference. A high degree of product purity can be attained when an adsorption process employs a moving-bed adsorption apparatus wherein the moving bed comprises adsorbent material which is countercurrently contacted by a multicomponent feedstream. When the adsorbent material remains stationary, such a process is described as a simulated countercurrent flow system. Essentially, the "countercurrent" flow in this system is created by allowing the adsorbent material in a chamber to contact fluid streams in different regions, as if a true countercurrent flow was created.

In the simulated countercurrent flow system, a chamber is divided into several zones and comprises in particular the following three zones: an adsorption zone, a (rectification) purification zone, and a desorption zone. Each zone may be subdivided into a plurality of serially interconnected sections, and each section may then be filled with adsorbent material. The zones are serially connected in this order, and a fluid stream is continuously circulated through the zones. Flow is maintained by circulating an effluent stream from an outlet in the rectification zone to an inlet in the adsorption zone. All points of introducing and withdrawing fluid streams are simultaneously shifted at predetermined intervals in a downstream direction; thus creating a simulated countercurrent flow.

The fluid stream is allowed to flow through the three serially and circularly interconnected zones, and at least one of the components, e.g., the desired component(s), of the feedstream will be adsorbed by contact with the adsorbent material. A desorbent stream is then introduced into the first section of the desorption zone. Feedstream is introduced to the first section of the adsorption zone while a raffinate stream comprising the less adsorbed component(s) and the excess desorbent, e.g., the unwanted component(s), of the feedstream is withdrawn from the adsorption zone. The fluid stream introduction and withdrawal points may then be shifted.

The fluid stream is interrupted, however, at a point between the desorption zone and the rectification zone. While a first portion of the desorption stream is flowing from the last section of the desorption zone, it is withdrawn from the chamber. This first portion contains little or no desorbent, but contains the product comprising the desired component(s). A second portion taken from the chamber at the same point contains pure quantities of the desired component(s), but at low concentrations in comparison to the first portion. This second portion may be introduced to a distillation column from which the desired component(s) is (are) recovered as product, and the distillate may be returned to the chamber.

SUMMARY OF THE INVENTION

By using a multiple grade flush in an adsorption separation process, the problems caused by the presence of unwanted components in conduits can be avoided. Further, the process of this invention may increase the capacity and efficiency of an adsorption process.

The process of the present invention separates a product from a multicomponent feedstream comprising at least one desired component to an adsorption apparatus. The at least one desired component may be an organic compound. Further, the organic compound may be a $C_8$ aromatic isomer, such as one selected from a group consisting of metaxylene, orthoxylene, and paraxylene.

In one embodiment, the process comprises the steps of:

introducing the feedstream through at least one fluid communication conduit into the apparatus;

flushing the at least one conduit with a sufficient quantity of at least one initial flushing medium comprising the at least one desired component in an initial concentration, such that feedstream residue is flushed from the at least one conduit into the apparatus by the at least one initial medium;

flushing the at least one conduit with a sufficient quantity of a final flushing medium comprising the at least one desired component in a final concentration, such that the final concentration is not less than the initial concentration and such that initial medium residue from the at least one initial medium is flushed from the conduit into the apparatus by the final medium; and withdrawing the product from the apparatus.

The apparatus may comprise a moving-bed adsorption apparatus or a simulated moving-bed adsorption apparatus. Further, the quantity of the initial medium may not be less than that sufficient to flush the feedstream residue from the conduit. Moreover, the apparatus may comprise a sieve chamber containing adsorbent material, e.g., adsorbent solids, such as charcoal, ion-exchange resins, silica gel, and the like, and the quantity of the initial medium may be sufficient to fill the apparatus to the sieve chamber capacity.

In another embodiment of the invention, the process may comprise the steps of:

introducing the feedstream through at least one fluid communication conduit into system comprising adsorbent material;

flushing the at least one conduit with a sufficient quantity of at least one initial flushing medium comprising the at least one desired component in an initial concentration, such that feedstream residue is flushed from the at least one conduit into the system by the at least one initial medium;

flushing the at least one conduit with a sufficient quantity of a final flushing medium comprising the at least one desired component in a final concentration, such that the final concentration is greater than the initial concentration, and such that initial medium residue from the at least one initial medium is flushed from the conduit into the system by the final medium;

withdrawing a raffinate stream from the system;

introducing a desorbent stream to the system;

withdrawing a combination comprised of the product and the desorbent from the system; and removing the product from the combination.

The system may also comprise a moving-bed adsorption apparatus or a simulated moving-bed adsorption apparatus. In addition, the quantity of the initial medium may not be less than that sufficient to flush the feedstream residue from the conduit. Moreover, the system may comprise a sieve chamber, and the quantity of the initial medium may be sufficient to fill the conduit.

In any of the embodiments of the process described above, the at least one initial medium may be drawn from the apparatus or system. In particular, an initial medium may be drawn from one the zones of the apparatus or system. Nevertheless, the at least one initial medium will typically be drawn from a source separate from the apparatus or the system. In preferred embodiments, the at least one conduit may be flushed twice, and a second flushing medium may be the final medium. Preferably, the final medium may comprise the product.

In yet another embodiment, the initial concentration of the at least one initial medium is continuously increased during the flushing of the at least one conduit until the initial concentration equals the final concentration. Preferably, this may be accomplished by adding the product to the at least one initial medium in gradually increasing amounts and decreasing proportionately flow from the source of the at least one initial medium.

This invention may increase the efficiency of adsorption apparatus or systems. It is a feature of this process that contaminants, such as feedstream residue, may be removed from fluid communication conduits by flushing them from the conduits into the apparatus or system with flushing media containing concentrations of the desired component (s) of the product which are higher than that of the feedstream. It is an advantage of this process that if the product is extracted through the same conduits that carried the feedstream, such as in a simulated moving-bed adsorption apparatus, extract will not be contaminated with feedstream residue.

Additionally, this invention may increase the capacity of an adsorption apparatus or system. It is an advantage of this process that excess capacity of the apparatus or system may be more fully utilized by purifying the solids with flushing media and flushing conduits with media containing the desired component(s). It is a feature of this process that fluid communication conduits may be flushed with media containing concentrations of a desired component or components higher than that of the feedstream, which may be drawn from a source other than the apparatus.

This invention also may increase the purity of the product obtained from an adsorption apparatus or system. It is a feature of this process that contaminants may be removed from conduits and from pores, channels, and holes in adsorbent solids, and conduits may be charged with the product. It is an advantage of the process that the product may be recycled through the apparatus or system, and excess apparatus or system capacity may be used to further separate other unwanted components of the feedstream remaining in the product.

Other advantages and features will be apparent when the detailed description of the invention and the drawings are considered.

DESCRIPTION OF PREFERRED
EMBODIMENTS OF THE INVENTION

Figure 1:
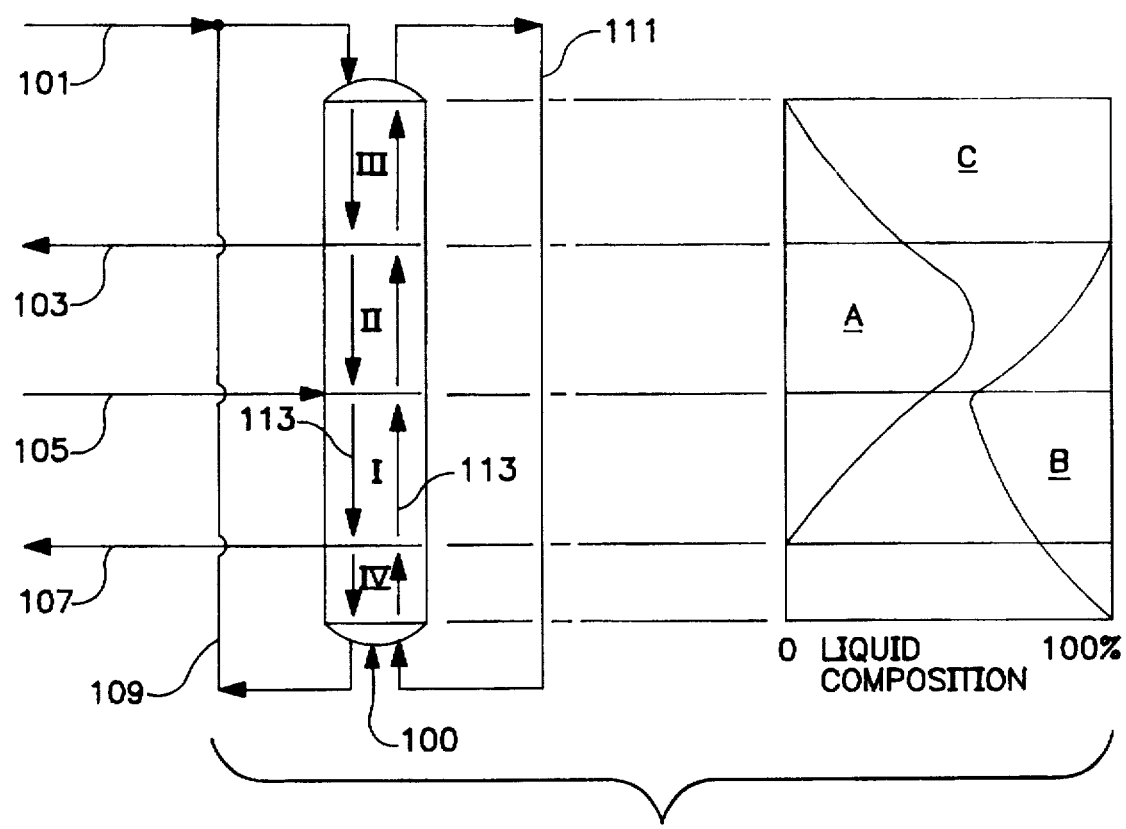
FIG. 1 is a combined flow diagram and composition chart which illustrates the relative flows and compositions of adsorbent solids and fluids in a simulated moving-bed adsorption process.

Referring to FIG. 1, the primary components of the fluid stream illustrated are desired product A, contaminate B, and desorbent C. Contaminate B may be a multicomponent fluid mixture. Desorbent C enters chamber 100 through fluid communication conduit 101. The feedstream comprised of desired product A and contaminate B enters chamber 100 through fluid communication conduit 105. Extract comprised of desired product A and desorbent C is extracted from chamber 100 through fluid communication conduit 103. Separation of desired product A from desorbent C may be effected further downstream of the currently discussed operation. Raffinate comprised of contaminate B and desorbent C is withdrawn through fluid communication conduit 107 from chamber 100. Fluid communication conduit 109 is a transfer fluid communication conduit to move fluid from the bottom to the top of chamber 100. A solid recycle stream 111 is simulated as flowing from the top of chamber 100 to the bottom. The simulated flows of the fluid and solid streams are illustrated within chamber 100 by the various fluid flows 113 and are essentially countercurrent flows.

Chamber 100 is divided into four operational zones, Zones I through IV. Zone I is an adsorption zone in which desired product A is adsorbed by the solids from the fluid. Zone II is a purification zone in which the contaminate B is removed from the pores, channels, or holes in and the spaces between the solids. Zone III is a desorption zone in which desired product A is desorbed from the solids. Zone IV also may include a buffer zone in which contaminate B is prevented from entering Zone III. The graph in FIG. 1 is a fluid composition chart showing the dynamics of the relative percentages of the three components in fluid moving through chamber 100. The composition of the fluid within chamber 100 is illustrated on a corresponding reference between chamber 100 and the graph. Although the zone boundaries are illustrated by straight horizontal lines, the zone boundaries actually may comprise curved demarcations which are dynamic during the process.

Figure 2:
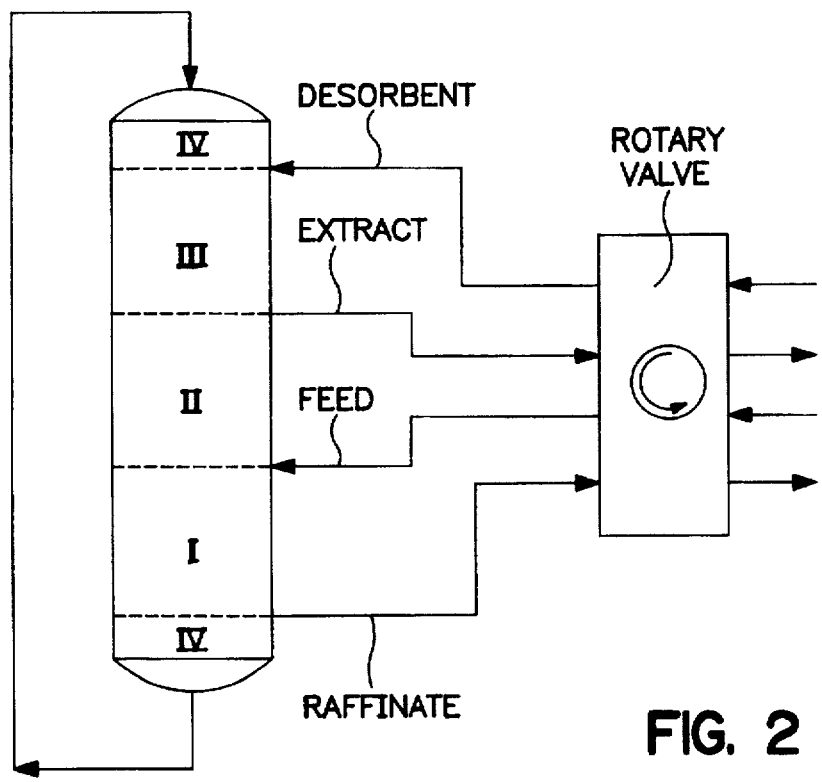
FIG. 2 depicts a simplified simulated moving-bed apparatus with a rotary valve for an adsorption process.

Referring to FIG. 2, which depicts a simplified simulated moving-bed apparatus with a rotary valve, countercurrent movement of the solids relative to the fluid streams is simulated by the use of the rotary valve. As the valve rotates, the zones previously discussed move through the column in a stepwise sequence due to the change in the stream flows through the valve. A preferred rotary valve for performing this invention is described in U.S. Pat. No. 3,205,166, the disclosure of which is incorporated herein by reference. In this arrangement, each fluid communication conduit connected to the chamber may serve a different function with each step rotation of the rotary valve. FIG. 2 further depicts the division of the chamber into four zones by the four function use of the fluid communication conduits. Thus, a first position of the rotary valve indicates the content and a direction for the flows through the separate fluid communication conduits, such as the connections and lines depicted. In a next position of the rotary valve, the line that is labelled "RAFFINATE" in the drawing now may be used for "FEED" with its direction of flow reversed, so that "FEED" flows from the valve to the chamber. The line which was previously designated the "FEED" line may now be used as the "EXTRACT" line. Such zone shifting occurs with each new position of the rotary valve. The result is that the Zones I, II, III, and IV are shifted inside the chamber in accordance with the change in the flow pattern. For a detailed description of the operation of rotary valves, see U.S. Pat. Nos. 3,040,777; 3,422,848; and 3,706,812. In the depiction of FIG. 2, only four uses of the fluid communication conduits are depicted; i.e., use as feed conduit, extraction conduit, raffinate conduit, and desorbent conduit. As discussed above, other uses are possible, such as for flushing to remove residue from the conduits.

Figure 3A:
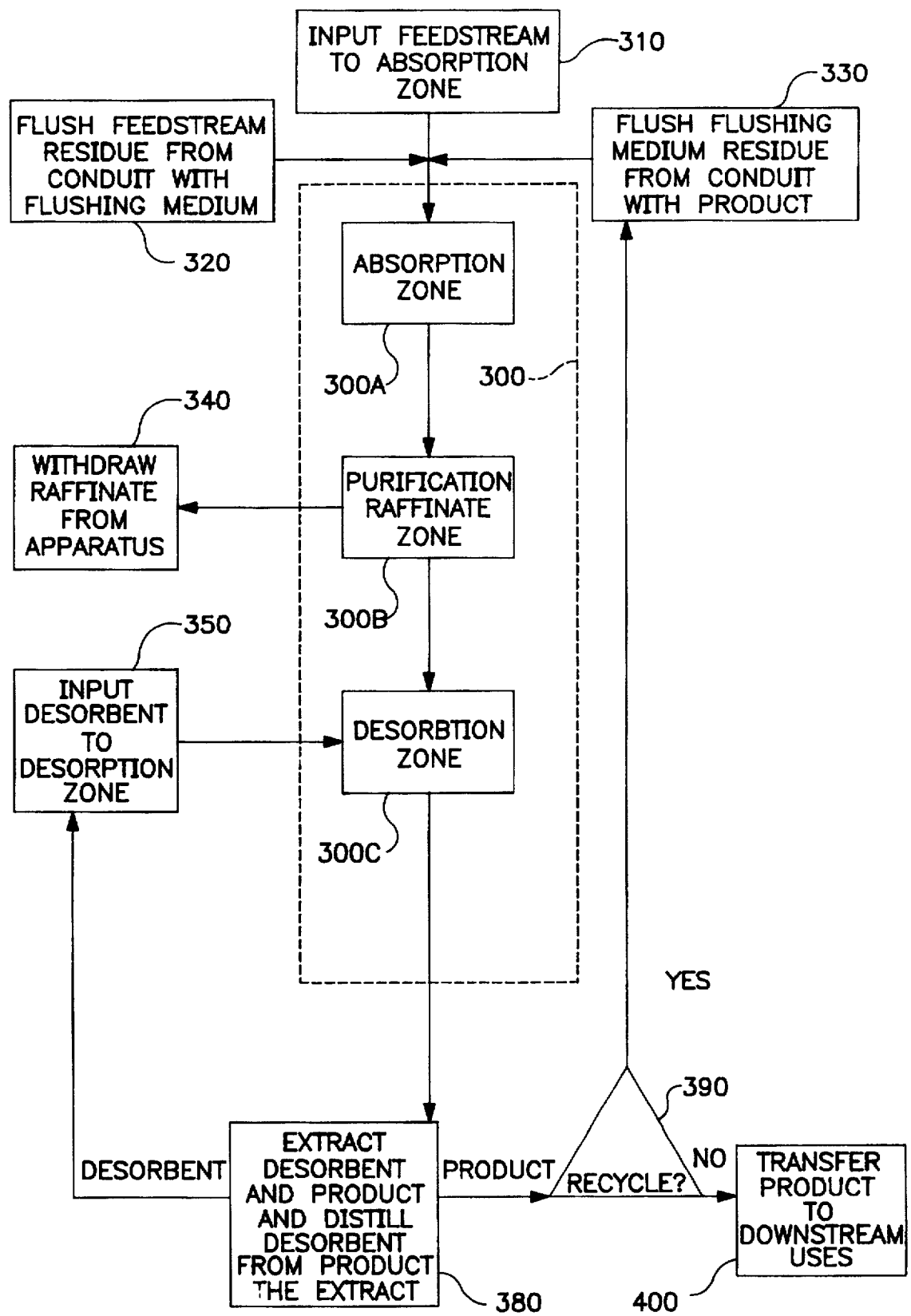
FIG. 3A and 3B are flow charts depicting the steps of preferred embodiments of the invention.

Referring to FIG. 3A, the flow chart depicts the relationship between the steps of an embodiment of the process of this invention and the zones of a simulated moving-bed adsorption apparatus 300, such as those disclosed in FIGS. 1–2. In step 310, a multicomponent feedstream is input to an adsorption zone 300A of apparatus 300 via a fluid communication conduit (not shown). While in adsorption zone 300A, a product comprising at least one desired component (not shown), such as a paraxylene, is adsorbed by adsorbent solids (not shown), such as crystalline aluminosilicate adsorbent, contained within apparatus 300.

In step 320, residue from the feedstream is flushed from the conduit by a first flushing medium. A sufficient quantity of the first flushing medium is used to flush all feedstream residue from the conduit and to fill a sieve chamber (not shown) of apparatus 300 to its capacity. In step 330, product is used to flush and residue of the first flushing medium from the conduit to apparatus 300. These three steps accomplish several functions. As discussed above, all residue of the feedstream and the first flushing medium is removed from the conduit, and the conduit is charged with the product. Preferably, the first flushing medium contains the desired component, and the addition of the flushing medium to adsorption zone 300A causes unwanted components to be driven from the pores, channels, or holes in and spaces between the solids and to be replaced, at least in part, by the desired components of the first flushing medium. Thus, the addition of the first flushing medium to the sieve chamber drives the unwanted components from apparatus 300, as indicated in step 330.

Once the product comprising the desired component(s) has been adsorbed by the solids, and the raffinate has been withdrawn from apparatus 300, the product can be recovered. In step 350, a desorbent, such as paradiethyl benzene (PDEB) or toluene or the like, is input to apparatus 300 in a desorption zone 300C. The desorbent more strongly bonds with the solids and replaces the product in the solids. Sufficient desorbent should be input, so that most or all of the product will be released from the solids.

In step 380, the product and any excess desorbent, i.e., extract, is removed from apparatus 300. Preferably, the desorbent will be sufficiently different from the product in boiling point or density, or both, such that the product and any excess desorbent can be easily separated from each other. It is further preferred that the desorbent's boiling point will be significantly different from that of the product, and the desorbent or the product may be easily distilled from the extract. Alternatively, however, the amount of excess desorbent may not be significant in comparison to the amount of product recovered, or the excess desorbent may constitute an unobjectionable component of the product. Nevertheless, if the desorbent is distilled from the extract, the desorbent will preferably be recycled for use in step 350.

Similarly, the product removed from the extract may be recycled in step 390. If the product is not to be recycled for using in flushing the residue of the first flushing medium from the conduit, the product will be sent to "downstream" uses, as depicted in step 400.

Figure 3B:
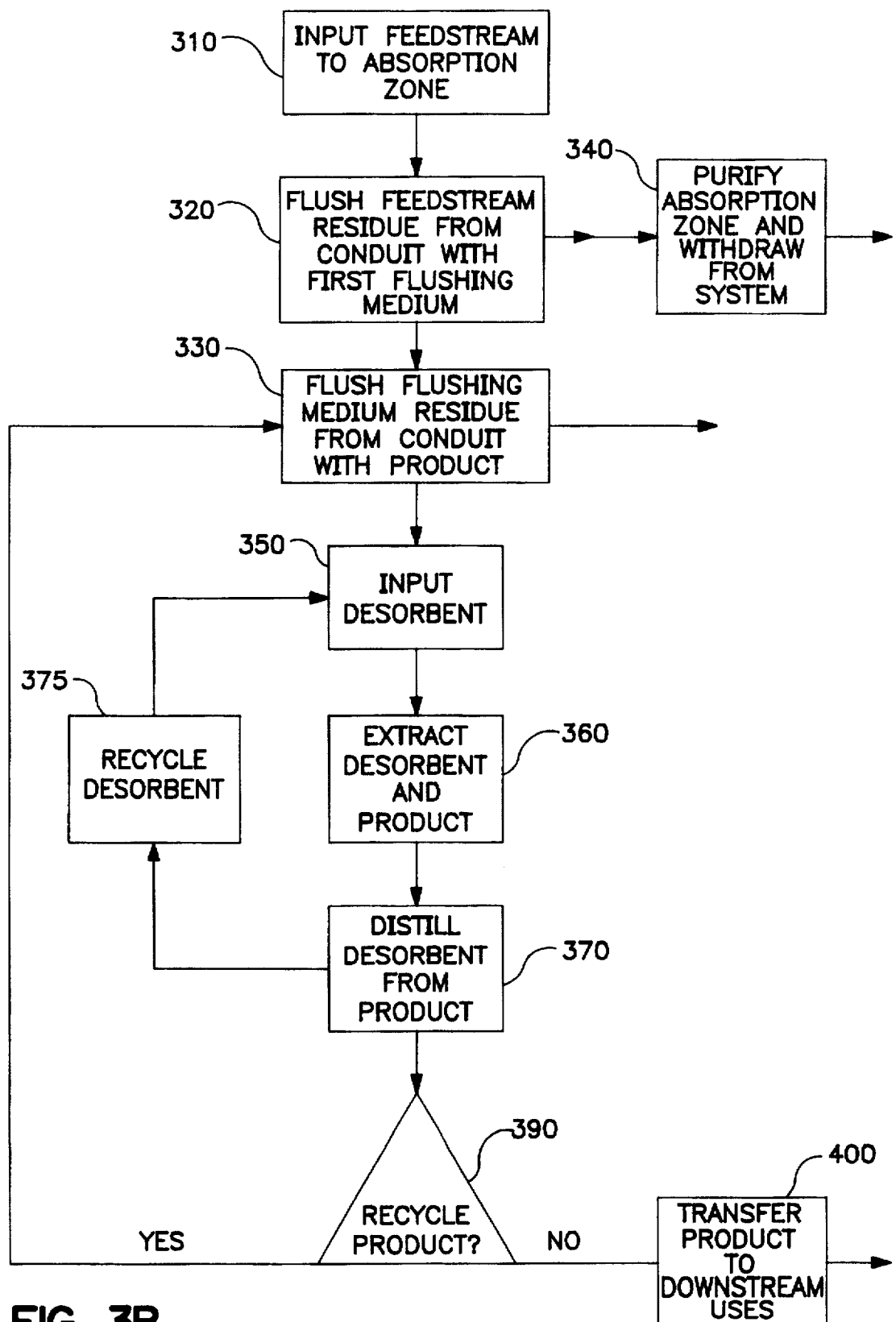

Referring to FIG. 3B, this flow chart also depicts the steps of a process of the invention, however, without regard to any particular adsorption apparatus. The steps common to FIGS. 3A and 3B are numbered accordingly. Nevertheless, the arrangement of these steps in FIG. 3B clarifies the relationships between them. As with FIGS. 3A, the process depicted in FIG. 3B begins with the input of a multicomponent feedstream to an adsorption zone via a fluid communication conduit, as indicated in step 310. Following the input of the feedstream, the conduit is flushed twice: first, by a first flushing medium to remove feedstream residue from the conduit, as indicated in step 320, and second, by the product to remove residue of the first flushing medium from the conduit, as indicated in step 330.

The flushing of the conduit causes the purification of the solids held in the adsorption zone, and the addition of fluid to an adsorption system drives the raffinate from the system, as indicated in step 340. Preferably, the first flushing medium is drawn from a source outside the adsorption system and comprises the desired component in a concentration greater than that of the feedstream, but less than that of the product. Therefore, the first flushing medium replaces many of the unwanted components held in the adsorbent material and adds to the purity of the product by driving those unwanted components from the system. Finally, by charging the conduit with the product, the amount of unwanted components carried over between process cycles is reduced.

After the flushing is complete and the raffinate has been withdrawn, desorbent is input to the system to desorb the product from the adsorbent material, as indicated by step 350. As noted above, sufficient desorbent must be input, such that as much product as possible is released from the adsorbent material. As indicated in steps 360 and 370, the product and any excess desorbent are then removed from the system and may be separated by distillation. Other methods of separation may be possible, but distillation is preferred. Once the product and the desorbent have been separated, the desorbent may be recycled to step 350, as indicated in step 375. Similarly, the product may also be recycled, as indicated in step 390, in which case the product will be used to flush the residue of the first flushing medium from the conduit, as indicated in step 330. If not, the product will be transferred for "downstream" uses as indicated in step 400.

Figure 4A:
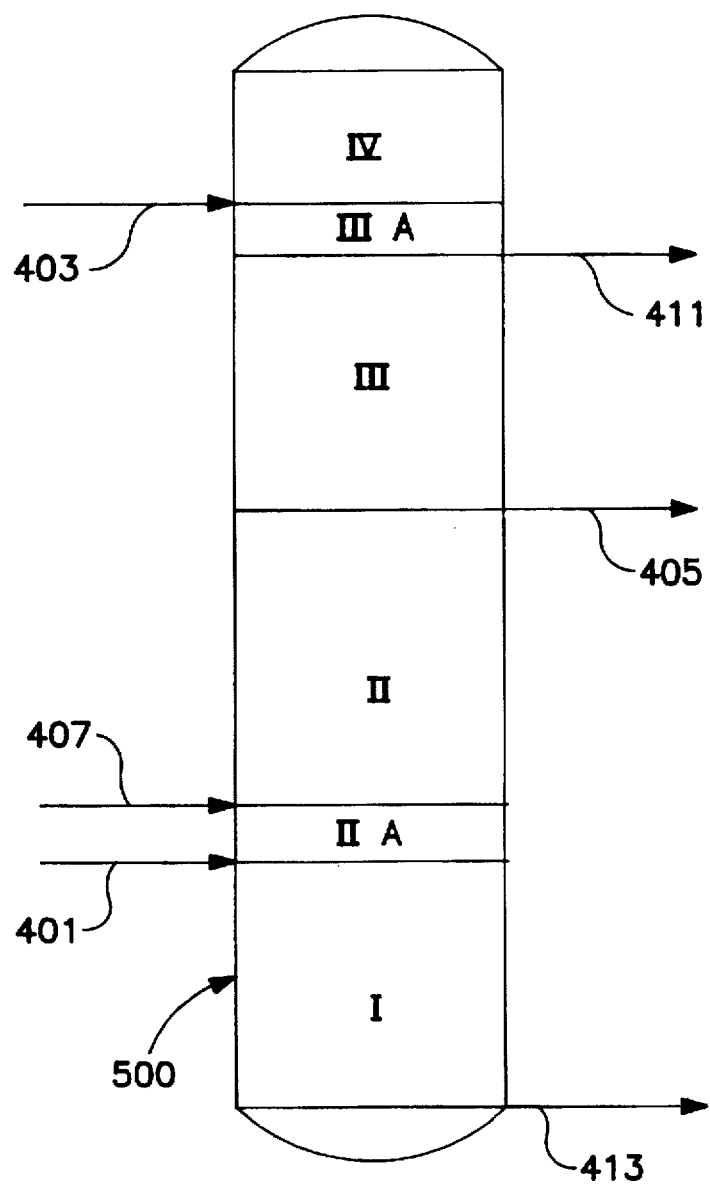
FIG. 4A and 4B depict the relative placement of the fluid communication conduits when a rotary valve is used in embodiments possessing sub-zones.
Figure 4B:
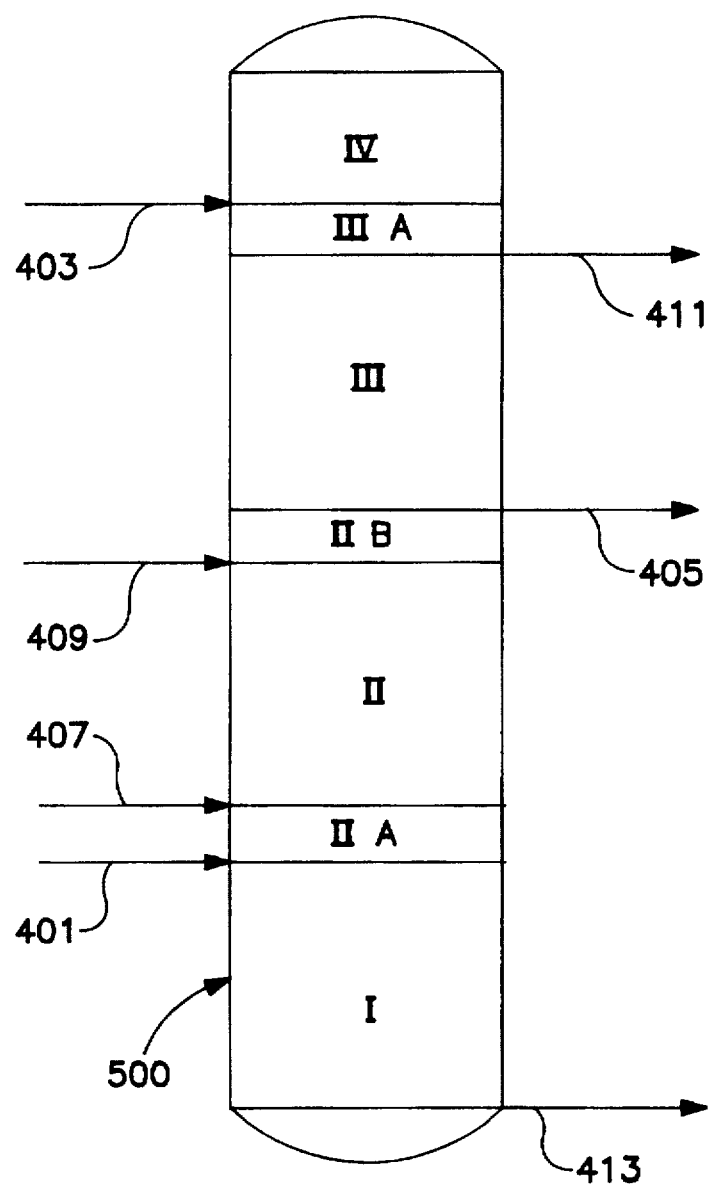

Referring to FIGS. 4A and 4B, the relative placement of the fluid communication conduits is depicted when a rotary valve is used in sub-zone embodiments. In FIG. 4A, chamber 500 is fed by feed fluid communication conduit 401, desorbent fluid communication conduit 403, and flushing fluid communication conduit 407. Extract fluid communication conduit 405, flushing fluid communication conduit 411, and raffinate fluid communication conduit 413 lead from chamber 500. These additional three fluid communication conduits create two sub-zones: Zones IIA and IIIA. Although a chamber, such as chamber 500, may have many more fluid communication conduits feeding fluids to it and leading from it, a six function rotary valve would operate fluid through the six fluid communication conduits depicted in FIG. 4A. Conversely, as depicted in FIG. 4B, a secondary flushing fluid communication conduit 409 may feed chamber 500, and a seven function rotary valve controls the fluid flow through seven conduits. The addition of secondary flushing fluid communication conduct 409 also creates an additional sub-zone, Zone IIB.

The rotary valve may be envisioned as operating in a rachet step manner. Nevertheless, such valves alone or in combination with the operation of other valves could provide a continuous flow or continuous concentration changes and not merely the step changes that either can provide alone. During the operation of the embodiment of FIG. 4A in a first valve position, fluid communication conduit 407 would supply flushing fluid and would be open. Valve means connected to conduit 407 could be opened or closed to effect a change in the flow of material through conduit 407. Accordingly, due to the operation of these valve means which can operate independently of the rotary valve, the concentration and flow rate of fluids through conduit 407 could be dynamic, i.e., changing during each single shift of the rotary valve. As the rotary valve shifts, the particular uses assigned to each of the conduits could also cycle or change, as discussed above.

Although multiple grades of paraxylene are illustrated in this example, it should be readily understood by those in the art that the benefits of this invention can be obtained without limit to the use of paraxylene. The medium or products involved in such process might be an organic compound, particularly an organic compound which is an aryl compound and more particularly, an aryl compound with at least one alkyl group attached to it. Therefore, other $C_8$ compounds can be used in this process. In adsorption processes intended to separate paraxylene from a multicomponent feedstream, however, a paraxylene flushing medium should be at least about 80% pure in the lower grade and at the desired paraxylene product purity in the higher grade. Although the sequence of relative concentrations may be reversed, this sequence is preferred. Other factors in the process also might be adjusted for its optimization, including variation in the flow rates for the feed, flushing, and withdrawal steps.

I claim:

1. A process for the separation of a product from a multicomponent feedstream to an adsorption apparatus, said product comprising at least one desired component, and said process comprising:

introducing said feedstream through at least one fluid communication conduit into said apparatus;

flushing said at least one conduit with a sufficient quantity of at least one initial flushing medium drawn from a first source and comprising said at least one desired component in an initial concentration, such that feedstream residue is flushed from said at least one conduit into said apparatus by said at least one initial medium;

flushing said at least one conduit with a sufficient quantity of a final flushing medium drawn from a second source and comprising said at least one desired component in a final concentration, such that said final concentration is greater than said initial concentration and such that initial medium residue from said at least one initial medium is flushed from said conduit into said conduit into said apparatus by said final medium; and withdrawing said product from said apparatus, wherein said first source is separate from said second source and at least one of said first source and said second source is separate from said apparatus.

2. The process of claim 1 wherein the quantity of said initial medium is greater than that sufficient to flush said feedstream residue from said conduit.

3. The process of claim 2 wherein said apparatus has a sieve chamber capacity and the quantity of said initial medium is sufficient to fill said apparatus to said sieve chamber capacity.

4. The process of claim 3 wherein said desired component is an organic compound.

5. The process of claim 4 wherein said organic compound is an $C_8$ aromatic isomer.

6. The process of claim 5 wherein said $C_8$ aromatic isomer selected from a group consisting of metaxylene, orthoxylene, and paraxylene.

7. The process of claim 1 wherein said apparatus has a sieve chamber capacity and the quantity of said initial medium is sufficient to fill said apparatus to said sieve chamber capacity.

8. The process of claim 1 wherein said desired component is an organic compound.

9. The process of claim 8 wherein said organic compound is an $C_8$ aromatic isomer.

10. The process of claim 9 wherein said $C_8$ aromatic isomer selected from a group consisting of metaxylene, orthoxylene, and paraxylene.

11. The process of claim 1 wherein said apparatus is a moving-bed adsorption apparatus.

12. The process of claim 1 wherein said apparatus is a simulated moving-bed adsorption apparatus.

13. The process of claim 12 wherein said at least one initial medium is drawn from said apparatus.

14. The process of claim 13 wherein said at least one conduit is flushed twice, and a second flushing medium is said final medium.

15. The process of claim 12 wherein said at least one conduit is flushed twice, and a second flushing medium is said final medium.

16. The process of claim 1 wherein said initial concentration is continuously increased until said initial concentration equals said final concentration.

17. The process of claim 1, wherein said desired component is paraxylene and said initial concentration is about 80% of said desired component.

18. The process of claim 1, wherein said at least one desired component is paraxylene and said final concentration is a desired paraxylene product purity.

19. The process of claim 1, wherein said adsorption apparatus includes an adsorbent material, such that said at least one desired component is adsorbed from said at least one initial flushing medium by said adsorbent material and said at least one initial flushing medium drives raffinate from said apparatus.

20. The process of claim 1, wherein said first source is separate from said apparatus.

21. The process of claim 1, wherein said adsorption apparatus includes an adsorbent material, such that said absorbent material has interstitial areas from within which said portion of said at least one initial flushing medium and said at least one unwanted fluid component are flushed.

22. A process for the separation of a product from a multicomponent feedstream to a simulated moving-bed adsorption apparatus, said product comprising paraxylene in a product concentration, and said process comprising:

introducing said feedstream through at least one fluid communication conduit into said apparatus;

flushing said at least one conduit with a sufficient quantity of a first flushing medium drawn from a first source and comprising paraxylene in a first concentration less than said paraxylene product purity concentration of said product such that feedstream residue is flushed from said at least one conduit into said apparatus by said at least one first flushing medium;

flushing said at least one conduit with a sufficient quantity of said product drawn from a second source in a paraxylene product purity concentration, such that any residue from said first medium is flushed from said conduit into said apparatus by said product; and withdrawing said product from said apparatus; wherein said first source is separate from said second source and at least one of said first source and said second source is separate from said apparatus.

23. The process of claim 22 wherein said first medium is drawn from said apparatus.

24. The process of claim 22, wherein said adsorption apparatus includes an adsorbent material, such that paraxylene is adsorbed from said first flushing medium by said adsorbent material and said first flushing medium drives raffinate from said apparatus.

25. The process of claim 22, wherein said first source is separate from said apparatus.

26. The process of claim 22, wherein said adsorption apparatus includes an adsorbent material, such that said absorbent material has interstitial areas from within which said portion of said at least one first flushing medium and said at least one unwanted fluid component are flushed.

27. A process for the separation of a product from a multicomponent feedstream, said product comprising at least one desired component, and said process comprising:

introducing said feedstream through at least one fluid communication conduit into a system comprising adsorbent material;

flushing said at least one conduit with a sufficient quantity of at least one initial flushing medium drawn from a first source and comprising said at least one desired component in an initial concentration, such that feedstream residue is flushed from said at least one conduit into said system by said at least one initial medium;

flushing said at least one conduit with a sufficient quantity of a final flushing medium drawn from a second source and comprising said at least one desired component in a final concentration, such that said final concentration is greater than said initial concentration, and such that initial medium residue from said at least one initial medium is flushed from said conduit into said system by said final medium;

withdrawing a raffinate stream from said system;

introducing a desorbent stream to said system;

withdrawing a combination comprised of said product and said desorbent from said system; and removing said product from said combination, wherein said first source is separate from said second source and at least one of said first source and said second source is separate from said system.

28. The process of claim 27 wherein the quantity of said initial medium is greater than that sufficient to flush said feedstream residue from said conduit.

29. The process of claim 28 wherein said system has a sieve chamber capacity and the quantity of said initial medium is sufficient to fill said system to said sieve chamber capacity.

30. The process of claim 29 wherein said desired component is an organic compound.

31. The process of claim 30 wherein said organic-compound is an $C_8$ aromatic isomer.

32. The process of claim 31 wherein said $C_8$ aromatic isomer selected from a group consisting of metaxylene, orthoxylene, and paraxylene.

33. The process of claim 27 wherein said system has a sieve chamber capacity and the quantity of said initial medium is sufficient to fill said system to said sieve chamber capacity.

34. The process of claim 27 wherein said desired component is an organic compound.

35. The process of claim 34 wherein said organic compound is an $C_8$ aromatic isomer.

36. The process of claim 35 wherein said $C_8$ aromatic isomer selected from a group consisting of metaxylene, orthoxylene, and paraxylene.

37. The process of claim 27 wherein said system comprises is a moving-bed adsorption apparatus.

38. The process of claim 27 wherein said system comprises a simulated moving bed adsorption apparatus.

39. The process of claim 38 wherein said at least one initial medium is drawn from said system.

40. The process of claim 39 wherein said at least one conduit is flushed twice, and a second flushing medium is said final medium.

41. The process of claim 38 wherein said at least one conduit is flushed twice, and a second flushing medium is said final medium.

42. The process of claim 27 wherein said initial concentration is continuously increased until said initial concentration equals said final concentration.

43. The process of claim 27, wherein said desired component is paraxylene and said initial concentration is about 80% of said desired component.

44. The process of claim 27, wherein said at least one desired component is paraxylene and said final concentration is a desired paraxylene product purity.

45. The process of claim 27, wherein said first source is separate from said system.

46. The process of claim 27, wherein said adsorption apparatus includes an adsorbent material, such that said absorbent material has interstitial areas from within which said portion of said at least one initial flushing medium and said at least one unwanted fluid component are flushed.

47. A process for the separation of a product from a multicomponent feedstream to an adsorption apparatus, said product comprising at least one desired component, and said process comprising:

introducing said feedstream through at least one fluid communication conduit into said apparatus, flushing said at least one conduit with a sufficient quantity of at least one initial flushing medium comprising said at least one desired component in an initial concentration, such that feedstream residue is flushed from said at least one conduit into said apparatus by said at least one initial medium;

flushing said at least one conduit with a sufficient quantity of a final flushing medium comprising a desorbent such that initial medium residue from said at least one initial medium is flushed from said conduit into said conduit into said apparatus by said final flushing medium; and withdrawing said product from said apparatus.

48. The process of claim 42, wherein said desired component is paraxylene and said initial concentration is about 80% of said desired component.

49. The process of claim 47, wherein said desorbent is selected from the group consisting of paradiethyl benzene and toluene.

* * * * *